US008658349B2

(12) United States Patent
Teich et al.

(10) Patent No.: US 8,658,349 B2
(45) Date of Patent: Feb. 25, 2014

(54) CELL ANALYSIS APPARATUS AND METHOD

(75) Inventors: Jay S. Teich, Berlin, MA (US); Andy C. Neilson, Sunapee, NH (US); Stephen C. Young, Chicopee, MA (US); Jim Orrell, Bothell, WA (US)

(73) Assignee: Seahorse Bioscience, Billerica, MA (US)

( * ) Notice: Subject to any disclaimer, the term of this patent is extended or adjusted under 35 U.S.C. 154(b) by 819 days.

(21) Appl. No.: 11/486,440

(22) Filed: Jul. 13, 2006

(65) Prior Publication Data

US 2008/0014571 A1   Jan. 17, 2008

(51) Int. Cl.
*C12Q 1/00* (2006.01)
(52) U.S. Cl.
USPC .......................................................... 435/4
(58) Field of Classification Search
USPC .......................................................... 435/4
See application file for complete search history.

(56) References Cited

U.S. PATENT DOCUMENTS

| | | |
|---|---|---|
| 4,065,357 A | 12/1977 | Groves |
| 4,256,832 A | 3/1981 | Findl et al. |
| 4,461,328 A | 7/1984 | Kenney |
| 4,498,510 A | 2/1985 | Minshew, Jr. et al. |
| 4,599,315 A | 7/1986 | Terasaki et al. |
| 4,711,851 A | 12/1987 | McNamara et al. |
| 4,879,097 A | 11/1989 | Whitehead et al. |
| 5,104,804 A | 4/1992 | Humphries et al. |
| 5,250,419 A | 10/1993 | Bernard et al. |
| 5,278,048 A | 1/1994 | Parce et al. |
| 5,459,300 A | 10/1995 | Kasman |
| 5,468,605 A | 11/1995 | Harris et al. |
| 5,495,850 A | 3/1996 | Zuckerman |
| 5,496,697 A | 3/1996 | Parce et al. |
| 5,536,662 A | 7/1996 | Humphries et al. |
| 5,567,598 A | 10/1996 | Stitt et al. |
| 5,728,541 A | 3/1998 | Kornblith |
| 5,766,875 A | 6/1998 | Hafeman et al. |
| 5,774,214 A | 6/1998 | Prettyjohns |
| 5,792,426 A | 8/1998 | Portmann et al. |
| 5,830,138 A | 11/1998 | Wilson |
| 5,959,297 A | 9/1999 | Weinberg et al. |
| 5,998,517 A | 12/1999 | Gentle, Jr. et al. |
| 6,030,917 A | 2/2000 | Weinberg et al. |
| 6,078,698 A | 6/2000 | Lorton et al. |
| 6,080,574 A | 6/2000 | Berndt |
| 6,083,761 A | 7/2000 | Kedar et al. |
| 6,146,967 A | 11/2000 | Thakur |
| D438,631 S | 3/2001 | Miller |
| D438,632 S | 3/2001 | Miller |
| D438,633 S | 3/2001 | Miller |
| 6,306,658 B1 | 10/2001 | Turner et al. |
| 6,376,233 B1 | 4/2002 | Wolf et al. |
| 6,380,605 B1 | 4/2002 | Verhaegen et al. |
| 6,395,506 B1 | 5/2002 | Pitner et al. |
| 6,395,555 B1 | 5/2002 | Wilson et al. |
| 6,416,967 B2 | 7/2002 | Kornblith |
| 6,468,736 B2 | 10/2002 | Brooker |
| 6,486,947 B2 | 11/2002 | Modlin et al. |
| 6,627,158 B1 | 9/2003 | Peltier |
| 6,653,124 B1 | 11/2003 | Freeman |
| 6,673,532 B2 | 1/2004 | Rao |
| 6,766,817 B2 | 7/2004 | da Silva et al. |
| 6,821,787 B2 | 11/2004 | Neilson et al. |
| 6,835,574 B2 | 12/2004 | Neilson et al. |
| 6,880,158 B1 | 4/2005 | Basso et al. |
| 6,881,584 B1 | 4/2005 | Lenhard et al. |
| 6,887,680 B2 | 5/2005 | Kornblith |
| 6,900,027 B1 | 5/2005 | Kornblith |
| 6,918,404 B2 | 7/2005 | da Silva |
| 6,933,129 B1 | 8/2005 | Kornblith |
| 7,066,586 B2 | 6/2006 | da Silva |
| 7,638,321 B2 | 12/2009 | Teich et al. |
| 7,795,012 B2 | 9/2010 | Lehmann et al. |
| 7,851,201 B2 | 12/2010 | Teich et al. |
| 2001/0051353 A1 | 12/2001 | Kornblith |
| 2002/0098592 A1 | 7/2002 | Neilson et al. |
| 2002/0098593 A1 | 7/2002 | Nelson et al. |
| 2002/0132360 A1 | 9/2002 | Neilson et al. |
| 2002/0146345 A1 | 10/2002 | Neilson et al. |
| 2002/0146836 A1 | 10/2002 | Neilson et al. |
| 2002/0168679 A1 | 11/2002 | Naus et al. |

(Continued)

FOREIGN PATENT DOCUMENTS

| | | |
|---|---|---|
| DE | 4016617 A1 | 11/1991 |
| DE | 4217868 A1 | 12/1993 |

(Continued)

OTHER PUBLICATIONS

Paitan et al. "Monitoring aromatic hydrocarbons by whole cell electrochemical biosensors", Analytical Biochemistry, 2004, 335:175-183.*
Deshpande et al. "Microplates with integrated oxygen sensing for medium optimization in animal cell culture", Cytotechnology, 2004, 46:1-8.*
Prokop et al. "NanoLiterBioReactor: long-term mammalian cell culture at nanofabricated scale", Biomedical Microdevices, 2004, 6(4):325-339.*
Andreescu et al. "Autonomous multielectrode system for monitoring the interactions of isoflavonoids with lung cancer cells", Anal. Chem. 2004, 76:2321-2330.*
Picture of How to adjust pH.*
Yang et al. "Reversible and repeatable linear local cell force response under large stretches", Experimental Cell Research, Apr. 2005, 305:42-50.*

(Continued)

*Primary Examiner* — Bin Shen
(74) *Attorney, Agent, or Firm* — Goodwin Procter LLP

(57) ABSTRACT

Devices and methods that measure one or more properties of a living cell culture that is contained in liquid media within a vessel, and typically analyzes plural cell cultures contained in plural vessels such as the wells of a multiwell microplate substantially in parallel. The devices incorporate a sensor that remains in equilibrium with, e.g., remains submerged within, the liquid cell media during the performance of a measurement and during addition of one or more cell affecting fluids such as solutions of potential drug compounds.

23 Claims, 9 Drawing Sheets

(56) References Cited

U.S. PATENT DOCUMENTS

| | | |
|---|---|---|
| 2002/0192638 A1 | 12/2002 | Kornblith |
| 2003/0059807 A1 | 3/2003 | Roach et al. |
| 2003/0162285 A1 | 8/2003 | Tajima |
| 2004/0023375 A1 | 2/2004 | Kornblith et al. |
| 2004/0072722 A1 | 4/2004 | Kornblith et al. |
| 2004/0077075 A1 | 4/2004 | Jensen et al. |
| 2004/0086888 A1 | 5/2004 | Kornblith et al. |
| 2004/0107986 A1 | 6/2004 | Neilson et al. |
| 2004/0110301 A1 | 6/2004 | Neilson et al. |
| 2004/0121454 A1 | 6/2004 | Jury et al. |
| 2004/0197905 A1 | 10/2004 | Hafeman |
| 2005/0054028 A1 | 3/2005 | Teich et al. |
| 2007/0037285 A1 | 2/2007 | Ehret et al. |
| 2010/0227385 A1 | 9/2010 | Teich et al. |

FOREIGN PATENT DOCUMENTS

| | | |
|---|---|---|
| DE | 4405375 A1 | 8/1995 |
| DE | 10136005 C1 | 11/2002 |
| DE | 10329983 | 3/2005 |
| EP | 0363262 A1 | 4/1990 |
| EP | 0722136 A2 | 7/1996 |
| EP | 0722136 A3 | 7/1996 |
| FR | 2792333 A1 | 10/2000 |
| WO | WO-95/22406 A1 | 8/1995 |
| WO | WO-98/15645 A1 | 4/1998 |
| WO | WO-99/55827 A1 | 11/1999 |
| WO | WO-99/60630 A1 | 11/1999 |
| WO | WO-00/32308 A2 | 6/2000 |
| WO | WO-00/36410 A1 | 6/2000 |
| WO | WO-01/85901 A2 | 11/2001 |
| WO | WO-01/85901 A3 | 11/2001 |
| WO | WO-02/02736 A1 | 1/2002 |
| WO | WO-02/08385 A1 | 1/2002 |
| WO | WO-02/11881 A1 | 2/2002 |
| WO | WO-02/061858 A2 | 8/2002 |
| WO | WO-02/061858 A3 | 8/2002 |
| WO | WO-02/072423 | 9/2002 |
| WO | WO-02/083852 A2 | 10/2002 |
| WO | WO-02/099386 A2 | 12/2002 |
| WO | WO-03/000557 A2 | 1/2003 |
| WO | WO-03/000557 A3 | 1/2003 |
| WO | WO-03/004596 A1 | 1/2003 |
| WO | WO-03/059518 A1 | 7/2003 |
| WO | WO-2004/065618 A2 | 8/2004 |
| WO | WO-2004/094060 | 11/2004 |

OTHER PUBLICATIONS

Linder et al. "Reagent-loaded cartridges for valveless and automated fluid delivery in microfluidic devices", Anal. Chem. 2005, 77:64-71.*
Beebe D.J., Mensing G.A., Walker G.M. (2002) "Physics and applications of microfluidics in biology." Annu. Rev. Biomed. Eng., 4, 261-86.
Beebe D.J., Moore J.S., Bauer J.M., Yu Q., Liu R.H., Devadoss, C., Jo B.H. (2000) Functional hydrogel structures for autonomous flow control inside microfluidic channels. Nature, 404, 588-590.
Bousse, L., Cohen, C., Nikiforov, T., Chow, A., Kopf-Sill, A.R., Dubrow, R. and Parce, J.W. (2000) "Electrokinetically Controlled Microfluidic Analysis Systems." Annu. Rev. Biophys. Biomol. Struct. 29, 155-181.
Brecht, A. & Gauglitz, G. "Optical probes and transducers," Biosensors and Bioelectronics, 10, p. 923-936, 1995.
Clark, L.C., Jr., Lyons, C., "Electrode Systems for Continuous Monitoring in Cardiovascular Surgery" NY Acad. Sci. 1962; 102: 29-45.
B. Cunningham, P. Li, B. Lin, J. Pepper, "Colorimetric resonant reflection as a direct biochemical assay technique," Sensors and Actuators B, vol. 81, p. 316-328, Jan. 5, 2002.
Flora K and J Brennan. "Comparison of Formats for the Development of Fiber-Optic Biosensors Utilizing Sol-Gel Derived Materials Entrapping Fluorescently-Labeled Proteins. Analyst," 1999, 124, 1455-1462.
Ge X, Kostov Y, and G Rao. "High Stability non-invasive autoclavable naked optical $CO_2$ sensor." 2003, Biosensor and Bioelectronics 18: 857-865.
Gesinski RM, Morrison JH, Toepfer JR. "Measurement of oxygen consumption of rat bone marrow cells by a polarographic method." J Appl Physiol. 1968; 24(6):751-754.
Hasselbrink, E.F., Jr., Shepodd ,T.J., Rehm, J. E.(2002) "High-pressure microfluidic control in lab-on-a-chip devices using mobile polymer monoliths" Anal Chem. 74, 4913-4918.
Hua S.Z., Sachs F., Yang D.X., Chopra H.D. (2002) "Microfluidic actuation using electrochemically generated bubbles." Anal Chem. 74, 6392-6396.
Huber et al., "Direct optical immunosensing (sensitivity and selectivity)," Sensors and Actuators B, 6, p. 122-126, 1992.
Jin et al., "A biosensor concept based on imaging ellipsometry for visualization of biomolecular interactions," Analytical Biochemistry, 232, p. 69-72, 1995.
Jordan, C.E., Corn, R.M. "Surface Plasmon Resonance Imaging Measurements of Electrostatic Biopolymer Adsorption onto Chemically Modified Gold Surfaces," Anal. Chem., 69:1449-1456 (1997).
Lähdesmäki I, Scampavia LD, Beeson C, and Ruzicka J. "Detection of Oxygen Consumption of Cultured Adherent Cells by Bead Injection Spectroscopy." Anal. Chem. 1999; 71: 5248-5252.
Lehmann, M, Baumann W, Brischwein M, Gahle H-J, Freund I, Ehret R, Dreschler S, Palzer H, Kleintges M, Sieben U and Wolf B. "Simultaneous measurement of cellular respiration and acidification with a single CMOS ISFET" 2001. Biosensors & Bioelectronics. 2001;16:195-203.
McConnell, H.M., Owicki, J.C., Parce, J.W., Miller, D.L., Baxter, G.T., Wada, H.G. and Pitchford, S. (1992) "The Cytosensor Microphysiometer: Biological Applications of Silicon Technology" Science 257: 1906-1912.
Metzger, R., Deglmann, C.J., Hoerrlein, S., Zapf, S. and Hilfrich, J. "Towards in-vitro prediction of an in-vitro cytostatic response of human tumor cells with a fast chemosensitivity assay" (2001) Toxicology 166, 97-108.
Morhard et al., "Immobilization of antibodies in micropatterns for cell detection by optical diffraction," Sensors and Actuators B, 70, p. 232-242, 2000.
Motterlini et. al., "Depression of Endothelial and Smooth Muscle Cell Oxygen Consumption by Endotoxin," American Journ. of Physio. vol. 275, No. 168 p. 776-782, Sep. 1998.
O'Riordan TC, Buckley D., Ogurtsov V, O'Connor R., Papkovsky DB "A cell viability assay based on monitoring respiration by optical oxygen sensing" Anal. Biochem. 2000; 278(2):221-227.
Owicki, J.C., Bousse, L.J., Hafeman, D.G., Kirk, G.L., Olson, J.D., Wada, H.G. and Parce, J.W. (1994) "The Light-Addressable Potentiometric Sensor: Principles and Biological Applications." Ann. Rev. Biophys. Biomol. Struct. 23: 87-113.
Panten U and Klein H. "$O_2$ consumption by isolated pancreatic islets, as measured in a Microincubation system with a Clark-type electrode." Endocrinology 1982; 111(5):1595-1600.
Parce W, Owicki J, Kercso K, Sigel G, Wada H, Muir V, Bousse L, Ross K, Sikic B, and McConnell H. 1989. "Detection of Cell-Affecting Agents with a Silicon Biosensor." Science. 1989; 246(4927):243-247.
Pattison R, Swamy J, Mendenhall B, Hwang C, and Frohlich B. "Measurement and Control of Dissolved Carbon Dioxide in Mammalian Cell Culture Processes Using an in Situ Fiber Optic Chemical Sensor." 2000. Biotechnology Prog. 16:769-774.
Pouli, A.E., Karagenc, N., Wasmeier, Christina, Hutton, J.C., Bright, N. Arden, S., Schofield, G.S., & Rutter, G.A. (1998) "A phogrin-aequorin chimaera to image $Ca^{2+}$ in the vicinity of secretory granules." Biochem. J., 330, 1399 - 1404.
Robiolio et al., "Oxygen diffusion and mitochondrial respiration in neuroblastoma cells," Am. J. Physiol. 256 (6 Pt 1):C1207-C1213 (Jun. 1989).
Rumsey et al., "Cellular Energetics and the Oxygen Dependence of Respiration in Cardiac Myocytes Isolated from Adult Rat" Journal of Biological Chemistry. 265(5):15392-15399. 1990.
Shenoy MA, Biaglow JE, Varnes ME, Hetzel FW. "Inhibition of cultured human tumor cell oxygen utilization by chlorpromazine." Adv Exp Med Biol.1983;159:359-68.
Thorsen, T., Maerkl, S.J. and Quake, S.R. (2002) Microfluidic Large-Scale Integration Science 298, 580-586.

(56) References Cited

OTHER PUBLICATIONS

Tolosa L, Kostov Y, Harms P, Rao G. "Noninvasive measurement of dissolved oxygen in shake flasks." Biotechnol Bioeng Dec. 5, 2002;80(5):594-7.

Unger, M.A., Chou, H-P, Thorsen, T., Scherer, A, and Quake, S.R. "Monolithic Microfabricated Valves and Pumps by Multilayer Soft Lithography"(2000) Science 288, 113-116.

Vanderkooi et. al., "An Optical Method for Measurement of Dioxygen Concentration Based upon Quenching of Phosphorescence," J. Biol. Chem., 262 (12):5476-5482 (Apr. 1987).

Wada, H.G. Indelicato, S.R., Meyer, L. Kitamura, T., Miyajima, A., Kirk, G., Muir, V.C. and Parce, J.W. (1993) "GM-CSF Triggers a Rapid Glucose Dependent Extracellular Acidification by TF-1 Cells: Evidence for Sodium/Proton Antiporter and PKC Mediated Activation of Acid Production" J. Cell Physiol. (1993) 154: 129-138.

Wiley, C and Beeson, C. (2002) "Continuous measurement of glucose utilization in heart myoblasts." Analytical Biochemistry 304, 139-146.

Wilson et al., "The Oxygen Dependence of Mitochondrial Oxidative Phosphorylation Measured by a New Optical Method for Measuring Oxygen Concentration," J. Biol. Chem., 263:2712-2718 (1988).

Wodnicka M, Guarino RD, Hemperly JJ, Timmins MR, Stitt D, Pitner JB. "Novel fluorescent technology platform for high throughput cytotoxicity and proliferation assays." Journal of Biomolecular Screening. 2000; 5:141-152.

Wolfbeis Os, 2002. "Fiber-Optic Chemical Sensors and Biosensors." Annal of Chem. 2002; 74:2663-2678.

Handbook of Fluorescent Probes and Research Products published by Molecular Probes, Inc., Eugene, Oregon, USA, http://www.probes.com/handbook/ (accessed Mar. 12, 2004), Table of Contents, 2 pages.

International Search Report for International Application No. PCT/US03/38294, Apr. 2004, 3 pages.

International Search Report and Written Opinion for PCT/US2004/029163, Mar. 2, 2005, 8 pages.

Seaver et al. "Hydrogen Peroxide Fluxes and Compartmentalization inside Growing *Eschericha coli*" Bacteriol., 2001, 183: 7182-7189.

Criddle et al. "Simultaneous Measurement of Metabolic Heat Rate, $CO_2$ Production, and $O_2$ Consumption by Microcalorimetry" Analytical Biochem. 1991, 194:413-417.

Ferguson et al. "Simultaneous monitoring of pH, $CO_2$, and $O_2$ using an optical imaging fiber" Analytica Chemica Acta, 1997, 340: 123-131.

"The Nature of ATP," ATP and Biological Energy, (as printed from Internet on Oct. 4, 2005, http://www.emc.maricopa.edu/faculty/farabee/BIOBK/BioBookATP.html).

Guppy, J. Cell Phys. 170:1-7 (1997).

Invitation to Pay Additional Fees & Partial Internation Search for International Application No. PCT/US2007/013998, mailed Feb. 1, 2008.

International Preliminary Report on Patentability for PCT/US2004/029163, Dec. 15, 2005, 15 pages.

International Search Report and Written Opinion for PCT/US2007/013998, Apr. 8, 2008, 19 pages.

Official Action in European Patent Application No. 04788615.5-1234, dated Mar. 12, 2008, 4 pages.

Office Action in Chinese Patent Application No. 200480029825, mailed Jul. 18, 2008 (translation).

International Preliminary Report on Patentability for PCT/US2007/013998, Jan. 22, 2009, 12 pages.

Office Action in Chinese Patent Application No. 200480029825, mailed Nov. 28, 2008 (translation).

Office Action in Indian Patent Application No. 1170/DELNP/2006, mailed Oct. 6, 2008 (translation).

Amano et al., "Measuring respiration of cultured cell with oxygen electrode as a metabolic indicator for drug screening," Human Cell 12(1):3-10 (1999).

Burd et al., "Tumor oxygenation and acidification are increased in melanoma xenografts after exposure to hyperglycemia and meta-iodo-benzylguanidine," Rediation Research 159:328-335 (2003).

Ekelund et al., "Microphysiometry: new technology for evaluation of anticancer drug activity in human tumor cells in vitro," Anti-Cancer Drugs 9:531-538 (1998).

Ainscow et al., "Top-down control analysis of ATP turnover, glycolysis and oxidative phosphorylation in rat hepatocytes," Eur. J. Biochem., 263(3):671-85 (Aug. 1999).

Andreescu, S. et al., "Advanced electrochemical sensors for cell cancer monitoring," Methods, vol. 37, pp. 84-93 (2005).

Buttgereit et al., "A hierarchy of ATP-consuming processes in mammalian cells," Biochem. J., Nov. 15, 1995;312 (Pt 1):163-7.

Gump et al., "TAT transduction: the molecular mechanism and therapeutic prospects," Trends Mol. Med., 13(10):443-48 (2007).

Jekabsons et al., "Bioenergetic analysis of cerebellar granule neurons undergoing apoptosis by potassium/serum deprivation," Cell Death Differ. 13(9):1595-610 (Sep. 2006) (Epub Jan. 20, 2006).

Karasinski, J. et al., "Detection and identification of bacteria using antibiotic susceptibility and a multi-array electrochemical sensor with pattern recognition," Biosensors and Bioelectronics, vol. 22, pp. 2643-2649 (2007).

Lou et al., "Mitochondrial uncouplers with an extraordinary dynamic range," Biochem J., 407(1):129-40 (Oct. 2007).

Scott et al., "Energy transduction in intact synaptosomes. Influence of plasma-membrane depolarization on the respiration and membrane potential of internal mitochondria determined in situ," Biochem. J. 186(1):21-33 (Jan. 1980).

Terada, "Uncouplers of oxidative phosphorylation," Environ. Health Perspect., 87:213-18 (1990).

Van der Gun et al., "Serum insensitive, intranuclear protein delivery by the multipurpose cationic lipid SAINT-2," J. Control Release, 123:228-238 (2007).

"How to Adjust pH Levels," Office Action mailed Sep. 28, 2010 in U.S. Appl. No. 11/486,440.

Official Action in European Patent Application No. 04788615.5-1234, dated Sep. 8, 2010, 6 pages.

Office Action in Chinese Patent Application No. 200780031522.6, dated Jul. 15, 2010 (translation).

Gatti et al., "Oxygen microoptodes: a new tool for oxygen measurments in aquatic animal ecology," Marine Biology, 2002, 140:1075-1085.

Maharbiz et al., "Silicon microbial bioreactor arrays," Poster 83, 1st Annual International IEEE-EMBA Special Topic Conference on Microtechnologies in Medicine & Biology, Oct. 12-14, Lyon, France.

Office Action in Chinese Patent Application No. 200780031522.6, dated Feb. 1, 2011.

\* cited by examiner

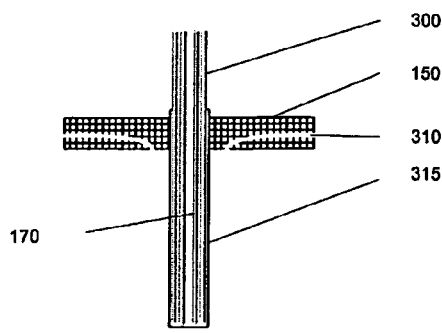
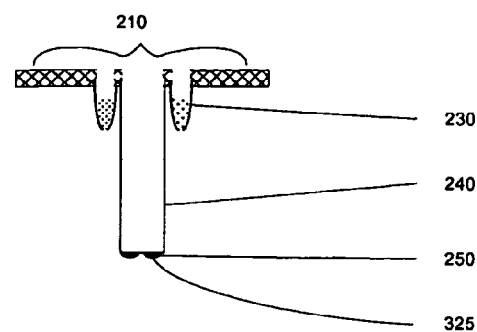
Fig 3　　　　　　　　　　Fig 4
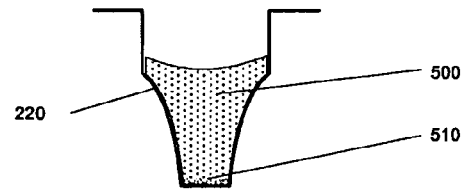
Fig 5
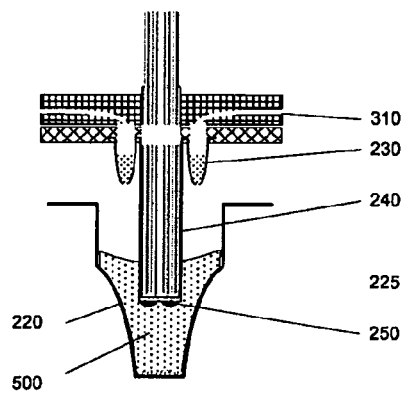
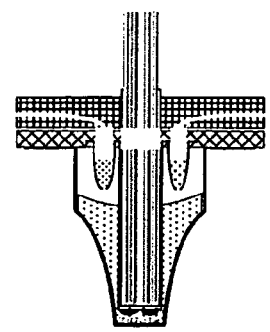
Fig 6a　　　　　　　　　　Fig 6b

FCCP Dose Response in HepG2 Cells

Low Dose Series
A=0.01µM, B=0.03µM, C=0.05µM, D=0.10µM (a)

Medium-1 Dose Series
A=0.10µM, B=0.30µM, C=0.60µM, D=1.20µM (b)

Medium-2 Dose Series
A=0.20µM, B=0.40µM, C=0.80µM, D=1.60µM (c)

High Dose Series
A=3.20µM, B=6.10µM, C=12.80µM, D=25.60µM (d)

CELL ANALYSIS APPARATUS AND METHOD

FIELD OF THE INVENTION

The invention relates generally to devices that measure one or more properties of a living cell culture that is contained in liquid media within a vessel, and typically analyzes plural cell cultures contained in plural vessels such as the wells of a multiwell microplate substantially in parallel. More specifically, the invention relates to devices that incorporate a sensor that remains in equilibrium with, e.g., remains submerged within, the liquid cell media during the performance of a measurement and during addition of one or more cell affecting fluids such as solutions of potential drug compounds.

BACKGROUND

Sensor probes may be used to measure a concentration of an analyte in a liquid media surrounding living cells as a means to interrogate the behavior of the cells and, in particular, to profile behavioral changes that are induced by exposure of the cells to candidate drug compounds. An example of an apparatus and method for making measurements of this type is described in U.S. Patent Publication No. 2005/0054028, the disclosure of which is incorporated by reference herein in its entirety.

One problem that may be encountered in using such a method is that an equilibration period may be required each time that the submersible sensor probe is placed in or otherwise exposed to the cell media. The equilibration period may be preferable or required to allow time for the probe to adjust to the temperature of the media, or for the sensor or its associated electronics to adapt to the difference between ambient air and the cell media. Such equilibration may require seconds, minutes, or hours depending, for example, on the sensor and measurement sensitivity desired.

The equilibration process may be undesirable to the user of the apparatus, because it may lengthen the time needed for analysis, and potentially may result in a measurement error if sequential equilibrations have differing characteristics.

A typical reason for removing a sensor probe from the cell media is to allow the addition of a test compound such as a drug candidate. This is particularly likely when the sensor probe is part of an assembly containing an array of probes, and when the test compound is delivered using an array of delivery devices such as pipettes, e.g., controlled and implemented by a robot.

SUMMARY OF THE INVENTION

The invention described herein provides a method, apparatus, instrument, cartridge, and measurement system for adding a test compound to a vessel, or multiple of the same or different test compounds to multiple wells of a microplate, while a sensor probe remains in equilibrium with, e.g., remains submerged within, the liquid contained within each vessel or well. Because the sensor probe remains submerged during compound delivery, equilibration time is reduced. Thus, a system and a method are provided for storing and dispensing a single preselected test compound, or preselected concentration of the compound per vessel or well. Furthermore, the storage and delivery apparatus may be fabricated from low cost materials, so that it may be discarded after use to eliminate cross-contamination from one use to another.

In another embodiment, the apparatus and method store and deliver multiple test compounds per well, preferably using a supply of compressed gas from a remote source to actuate the compound delivery. In a preferred embodiment, both the sensor probe and test compound delivery structure are incorporated within a single disposable cartridge. A pneumatic multiplexer is also described that, when temporarily attached to the cartridge, allows a single actuator to initiate the delivery of test compound from multiple ports using a supply of compressed gas from a remote source.

In one aspect, the invention features a cartridge adapted to mate with a multiwell plate having a plurality of wells. The cartridge includes a substantially planar element having a plurality of regions corresponding to a common number of respective openings of the wells in the multiwell plate. At least one port is formed in the cartridge in at least one region, the port being adapted to deliver a test fluid, e.g., an aqueous solution of a candidate drug compound, to the respective well. The cartridge also includes at least one of a) a sensor or portion thereof adapted to analyze a constituent in a well and b) an aperture adapted to receive a sensor located in a sub region of the at least one region of the cartridge.

The apparatus and method may include one or more of the following features. The port forms a capillary aperture to retain test fluid in the port absent an external force. The external force may be a positive pressure differential force, a negative pressure differential force, and/or a centrifugal force. The sensor (or portion thereof or aperture adapted to receive a sensor) preferably is compliantly attached to the planar element so as to accommodate slight misalignment of the probe structure with the wells of microplate. A second port is formed in the cartridge in the at least one region, the second port being adapted to deliver a second test fluid to the respective well. The second test fluid may be the same or different from the first test fluid, or a different concentration of the previously deposited fluid. The cartridge may form a cover for the multiwell plate to reduce contamination and/or evaporation of sample in the multiwell plate. Preferably, at least one port, preferably multiple ports, e.g., four ports, are formed in multiple regions of the cartridge, and at least one of the sensor and the aperture adapted to receive the sensor is located in each region. Multiple ports in different regions may be in fluidic communication. A second port may be formed in the cartridge in every region. The second ports also may be in fluidic communication with each other and not in fluidic communication with other ports. A common number of ports may be formed in every region of the cartridge, and a common number of sets of ports. A multiplexer may be in fluidic communication with each set of ports. The multiplexer may be adapted to connect to a single pneumatic source to permit delivering fluid to the wells sequentially from each set of ports.

In preferred embodiments, the sensor is adapted to analyze (determine the presence or concentration of) an extracellular constituent in a well, such as $CO_2$, $O_2$, $Ca^{++}$, $H^+$, or a consumed or secreted cellular metabolite. The aperture adapted to receive the sensor may comprise a sensor sleeve structure having a surface proximal to a well of the multiwell plate. Disposed on the surface is a fluorophore having fluorescent properties dependant on at least one of the presence and the concentration of a constituent in the well. The sensor sleeve may include an elongate housing for receiving a wave guide for at least one of stimulating the fluorophore and for receiving fluorescent emissions from the fluorophore.

In another aspect, the invention features apparatus comprising a system for analyzing cells. The apparatus includes a stage adapted to receive and position a plate having a plurality of wells and a cartridge which mates with the multiwell plate. The apparatus also includes an elevator mechanism adapted to move the cartridge relative to the stage or the plate to dispose the sensor in the well, typically multiple sensors in multiple wells simultaneously. The cartridge comprises a substantially planar element having a plurality of regions corresponding to a number of respective openings of the wells in the multiwell plate, with each region defining at least one port adapted to deliver a test fluid to the respective well. At least one sensor adapted to analyze a constituent in a well is located in each region of the cartridge.

The apparatus may include one or a combination of the following features: A pressure source adapted to be mated fluidically with the cartridge, to deliver the test fluid from a port in the cartridge to a well; a multiplexer disposed between the pressure source and the cartridge, the multiplexer being adapted to be in fluidic communication with a plurality of ports formed in the cartridge. The multiplexer may be in fluidic communication selectively with exclusive sets of ports formed in the cartridge; a controller to control the elevator mechanism, the multiplexer, and/or the pressure source to enable delivery of test fluid from a given port or set of ports to a corresponding well or set of wells when an associated sensor is disposed in the well.

An array of sensors corresponding to an array of wells may be and preferably are integral with the cartridge, but may also be separate elements mated with and disposed within apertures formed in the cartridge. The sensor array preferably is mounted compliantly relative to the well plate. The sensors preferably comprise a fluorophore having fluorescent properties dependant on at least one of the presence and concentration of a constituent in the well, and a wave guide for stimulating the fluorophore and for receiving fluorescent emissions from the fluorophore.

In another aspect, the invention features a method of analyzing cells disposed in media in a multiwell plate. The method includes disposing as least a portion of a sensor in media in a well in the multiwell plate, analyzing a constituent related to the cells within the media in the well, delivering a test fluid to the well while the sensor remains disposed in the media in the well, and further analyzing the constituent to determine any change therein.

One or more of the following features may be included. The analyzing step may include analyzing respective constituents related to respective cells within media in respective wells. The respective constituents may be the same constituent. The delivering step includes delivering respective test fluids to the respective wells while respective sensors remains disposed within media in respective wells. The respective test fluids may include the same test fluid. The step of analyzing step includes analyzing respective constituents related to respective cells within media in respective wells to determine any respective changes therein. The delivering step and the further analyzing step may be repeated. A different test fluid or an additional aliquot of the same test fluid may be delivered between measurements. The method may include substantially maintaining equilibration between the sensor and the media during the delivery step or maintaining thermal equilibrium between the test fluid and the media during the delivery step.

In still another aspect, the invention features an instrument for analysis of cells disposed in a microplate. The instrument includes a stage for positioning a microplate and a plurality of probes, each probe positioned for acquiring data from respective wells in the microplate. The instrument also includes a controller for effecting the addition of one or more reagents to one or more of the wells of the microplate; and a system in communication with the controller and the probes including a graphical user interface residing on a computer. The graphical user interface is configured to receive instructions for the design of a multi-well experiment and to receive the data acquired by the probes in response to the execution of the multi-well experiment.

One or more of the following features may be included. The instructions describe the addition of one or more selected solutions of potential cell affecting substances to one or more of the wells. The graphical user interface includes a plurality of display areas, each area being attributed to one of the wells. The display areas include at least one parameter of the experiment. The display areas include at least one result of the experiment, the results being based at least in part on the data acquired by the probes. The plurality of display areas are disposed about a screen, the screen representing the microplate. The data acquired by the probes in response to the execution of the multi-well experiment includes data spanning multiple microplates, and the graphical user interface is further configured to display data from each microplate on a separate respective screen. The system includes an analysis engine configured to produce one or more graphical representations of the data acquired by the probes. The analysis engine is configured to perform statistical analysis on the data acquired by the probes. The instrument includes a communications module for transmitting the experiment instructions and the data acquired by the probes among the controller, the probes and the system. The communication among the controller, the probes and the system is carried out over a digital communications network. The communications network includes a local-area network, a wide-area network, an intranet, the Internet, and/or combinations thereof.

In another aspect, the invention features an instrument for analysis of reactions of cells disposed in a microplate. The instrument includes a stage for positioning a microplate, and a sensor probe positionable for acquiring data from respective wells in the microplate. The instrument also includes a system in communication with the probe including a graphical user interface residing on a computer and including a plurality of display areas, each area being attributed to one of the wells. The graphical user interface is configured to receive instructions written in respective areas attributed to one of the wells for the design of a multi-well experiment, and receive the data acquired by the sensors in response to the execution of the multi-well experiment for display in a respective area attributed to one of the wells.

One or more of the following features may be included. The display areas further include at least one parameter of the experiment. The display areas further include at least one result of the experiment, the result being based at least in part on the data acquired by the probes. The instrument includes a plurality of the probes. The probe reads at least one of optical density, luminescence, phosphorescence, and fluorescence. The instrument includes a controller for effecting the addition of at least one reagent to at least one of the wells, the user interface being configured to receive instructions for the design of a multi-well experiment. The instrument includes a single probe addressable to at least one of a well and a subset of wells. The system includes an analysis engine configured to produce one or more graphical representations of the acquired data. The analysis engine is configured to perform statistical analysis on the acquired data.

The instrument operating software enables the use, by both a desktop application and the instrument operating software, of a file that contains both experiment design information entered by the user (e.g., what material is in each well, etc.) and results data entered by the instrument. An embedded analysis tool may be included. The instrument operating software may be incorporated within a third party spreadsheet package such as Excel.

BRIEF DESCRIPTION OF THE DRAWINGS

FIGS. 3, 4 and 5 together present a schematic, isolated, partial cross-sectional, exploded view of one region of an embodiment of the apparatus of the present invention, illustrating (FIG. 3) a portion of a sensor probe structure including an internal optical fiber bundle for light transmission to and from fluorescent sensor spots, the probe structures being inserted through a pneumatic multiplexer; the cartridge (FIG. 4—see figures FIGS. 2a and 2b) illustrating spots of fluorescent sensors disposed on an outside of a sleeve defining an aperture for receiving the portion of a sensor probe of FIG. 3, and two ports adapted to deliver a test fluid to a single well of the multiwell plate; and a single well of the multiwell plate (FIG. 5, see FIGS. 2a and 2b);

FIGS. 6a and 6b are schematic cross-sectional views of the probe structure, cartridge portion, and single well of FIGS. 3, 4, and 5 in a partially raised (mix or equilibrate) position and in a lowered (data gathering) position;

DETAILED DESCRIPTION

The invention enables the measurement of one or more properties of living cells that are disposed in, for example, a well of a multiwell microplate. Embodiments of the invention include a sensor, preferably a submersible sensor that enables fast sensor stabilization, thereby increasing measurement throughput. The disclosed compound storage and delivery apparatus, pneumatic multiplexer, structure for adding fluids to subsets or all of multiple wells simultaneously, and sensor structure permitting non destructive measurement of the effect of addition of exogenous fluid to respective wells, in combination with the ability to make and repeat measurements rapidly, results in the provision of a low cost per test, high throughput cellular assay system ideal, e.g., for drug discovery applications. Furthermore, the invention provides a cartridge structure which permits repeated use of the apparatus for disparate cellular assays without requiring intermediate cleaning, and while eliminating the possibility of cross contamination between tests. Still further, the invention provides software for designing and implementing multi-well cellular assays run in parallel, and for receiving and analyzing the generated data that is intuitive and easy to use, permits multiple scientists to design and execute multiwell parallel assays during the same time period, and preferably is based on a spreadsheet program of the type well understood by scientists and easily integrated with sophisticated LIMS systems.

Figure 1:
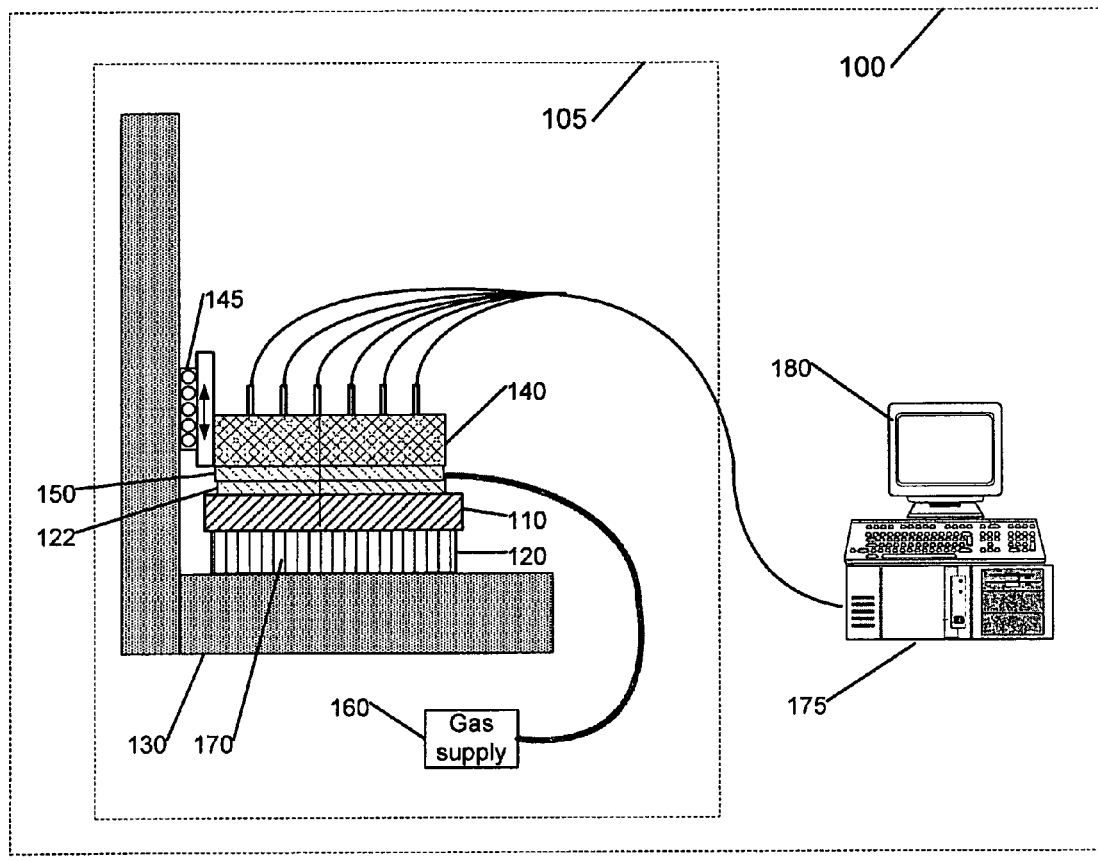
FIG. 1 is a schematic illustration of a complete measurement system and apparatus in accordance with one embodiment of the invention.

Referring to FIG. 1, the apparatus 100 is illustrated schematically. It comprises a compound storage and delivery apparatus in a housing 105 (shown in dashed lines) that includes a cartridge 110 defining a plurality of apertures for receiving sensor structures and a plurality of fluid ports (shown in detail in FIGS. 2a and 2b) compliantly mounted, and a stage or base 130 adapted to receive a multiwell plate 120, e.g., a cell culture plate. The cartridge 110 is disposed above, and adapted to mate with, the multiwell plate 120. The cartridge 110 optionally is held by a cartridge holder 122 adapted to receive the cartridge 110. The compound storage and delivery apparatus 105 also includes a mounting block 140, which can reciprocate as shown by the double headed arrow, preferably powered by a motor (not shown), including an elevator mechanism 145. The elevator mechanism 145 is adapted to move the cartridge 110 relative to the stage 130, or well plate 120. The mounting block includes a gas multiplexer 150 attached to a pressure source, e.g., gas supply or gas reservoir 160. The gas supply 160 is in fluid communication with the cartridge, and is used to impel the delivery of test fluid from a port in the cartridge to a well in the multiwell plate 120 as disclosed below. A plurality of sensor probes 170 are adapted for insertion into the plurality of apertures in the cartridge 110, and may be used to gather data indicative of the state of cells disposed in wells in the multiwell plate 120.

The compound storage and delivery apparatus 105 is controlled by a controller 175, that may be integrated with a computer 180, that may control the elevator mechanism, the multiplexer, and the pressure source. The controller 175 may, thereby, permit delivery of a test fluid from a port to a corresponding well when an associated sensor is disposed in the well.

Figure 2A:
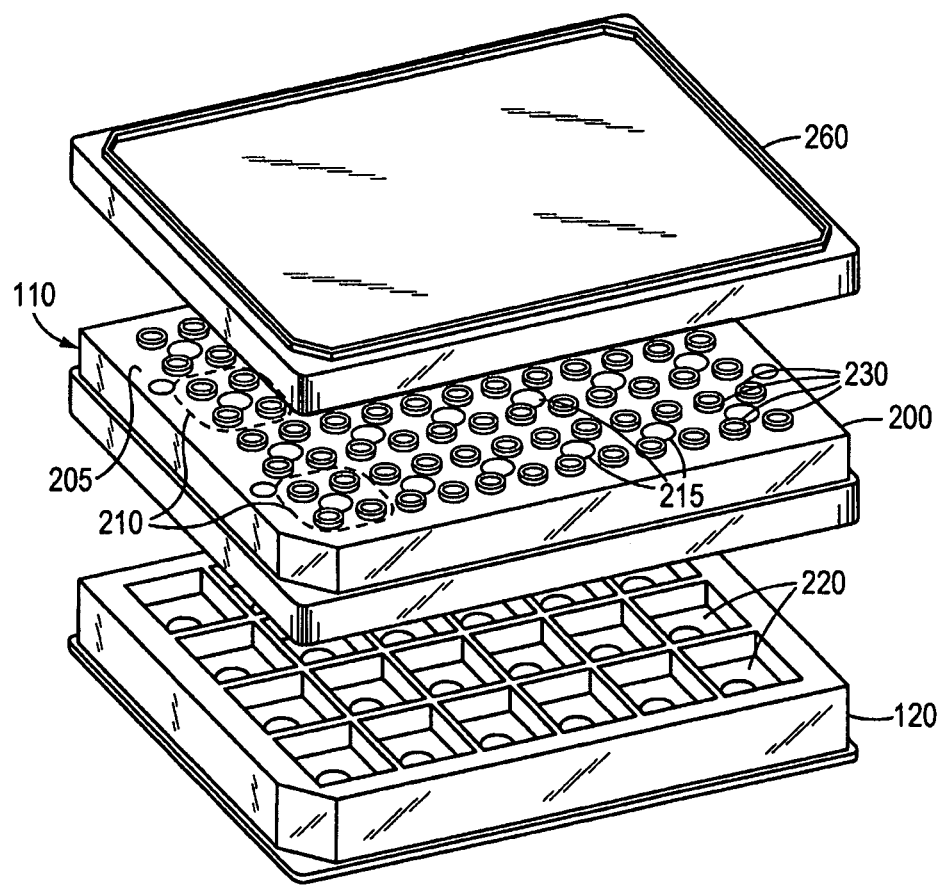
FIGS. 2a and 2b are upright and inverted (respectively) exploded perspective views of a multiwell plate and a covered cartridge adapted to mate with the multiwell plate in accordance with one embodiment of the invention.
Figure 2B:
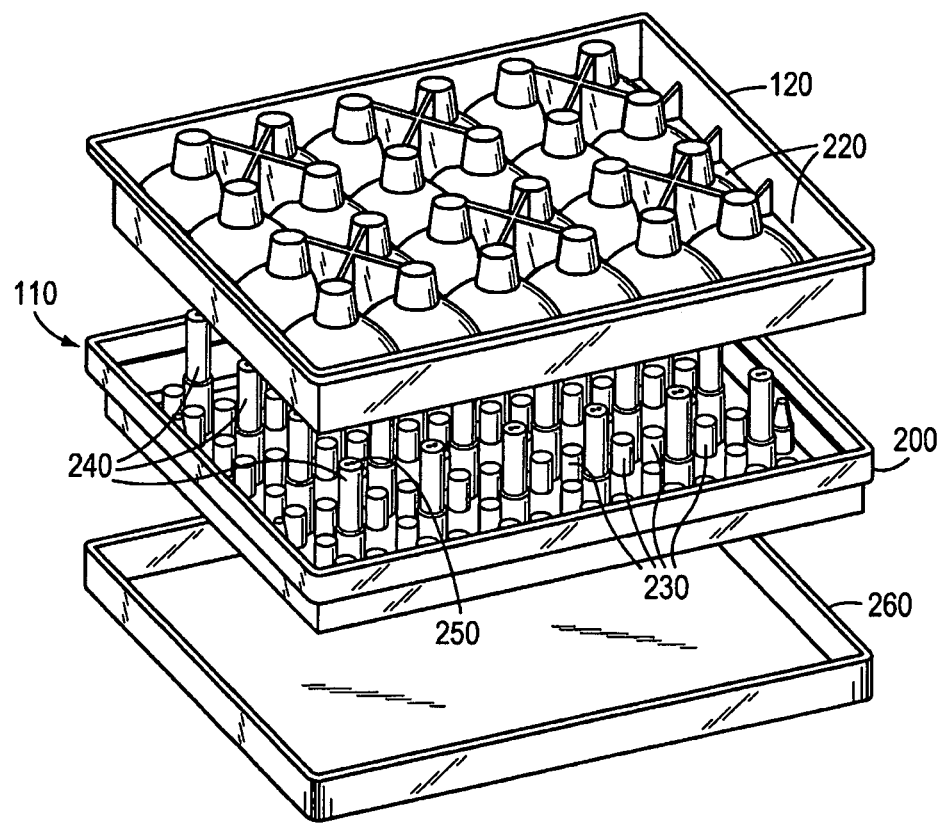

FIGS. 2a and 2b illustrate the currently preferred form of the cartridge 110 and microplate 120, and how they relate to each other. The cartridge is a generally planar element comprising a frame 200 made, e.g., from molded plastics. Planar surface 205 defines a plurality of regions 210 that correspond to, i.e., register with, a number of the respective openings of a plurality of wells 220 defined in the multiwell plate 120. Within each of these regions 210, in the depicted embodiment, the planar element defines first, second, third, and fourth ports 230, which serve as test compound reservoirs, and a central aperture 215 to a sleeve 240. Each of the ports is adapted to hold and to release on demand a test fluid to the respective well 220 beneath it. The ports 230 are sized and positioned so that groups of four ports may be positioned over the wells 220, and test fluid from any one of the four ports may be delivered to a respective well 220. In other embodiments the number of ports in each region may be less than four or greater than four. The ports 230 and sleeves 240 may be compliantly mounted relative to the microplate 120 so as to permit it to nest within the microplate by accommodating lateral movement. The construction of the microplate to include compliant regions permits its manufacture to looser tolerances, and permits the cartridge to be used with slightly differently dimensioned microplates. Compliance can be achieved, for example, by using an elastomeric polymer to form planar element 205, so as to permit relative movement between frame 200 and the sleeves and ports in each region.

Each of the ports 230 may have a cylindrical, conic or cubic shape, open through planar element 200 at the top, and closed at the bottom except for a small hole, i.e., a capillary aperture, typically centered within the bottom surface. The capillary aperture is adapted to retain test fluid in the port, e.g., by surface tension, absent an external force, such as a positive pressure differential force, a negative pressure differential force, or possibly a centrifugal force. Each port may be fabricated from a polymer material that is impervious to test compounds, or from any other solid material. When configured for use with a multiwell microplate 120, the liquid volume contained by each port may range from 500 µl to as little as 2 µl, although volumes outside this range are contemplated.

In the depicted embodiment, multiwell plate 120 has 24 wells. The number of wells 220 in a plate may vary from 1 to several thousand. In other embodiments, a single well of nearly any size may be fabricated, or multiple wells may be fabricated, or multiple wells may be fabricated in a one- or two-dimensional arrangement. In one embodiment, a two-dimensional pattern of wells corresponding to the pattern and dimensions of a microplate, as described by the Society for Biomolecular Screening standards for microplates ("SBS-1 Footprints" and "SBS-4 Well Positions," both full proposed standards updated May 20, 2003), and containing a total of 12, 24, 96, 384, 1536, or any other number of individual wells may be fabricated.

Referring to FIG. 2b, in each region of the cartridge 110, disposed between and associated with one or more ports 230, is a submersible sensor sleeve or barrier 240, adapted to be disposed in the corresponding well 220. Sensor sleeve 240 may have one or more sensors 250 disposed on a lower surface 255 thereof for insertion into media in a well 220. One example of a sensor for this purpose is a fluorescent indicator, such as an oxygen-quenched fluorophore, embedded in an oxygen permeable substance, such as silicone rubber. The fluorophore has fluorescent properties dependant on the presence and/or concentration of a constituent in the well 220. Other types of known sensors may be used, such as electrochemical sensors, Clark electrodes, etc. Sensor sleeve 240 may define an aperture and an internal volume adapted to receive a sensor. Examples of the types of sensors that may be used are described below with reference to FIG. 3.

The cartridge 110 may be attached to the sensor sleeve, or may be located proximal to the sleeve without attachment, to allow independent movement. The cartridge 110 may include an array of compound storage and delivery ports assembled into a single unit and associated with a similar array of sensor sleeves.

The apparatus may also feature a removable cover 260 for the cartridge 110 or for multiwell plate 120. The configuration of cartridge 110 as a cover for multiwell plate 120 may help prevent evaporation or contamination of a sample or media disposed in wells 220. The cover 260 may also be configured to fit over the cartridge 110 thereby to reduce possible contamination or evaporation of fluids disposed in the ports 230 of the cartridge 110.

Referring also to FIG. 3 through 6b, details of preferred relationship of parts is illustrated. FIG. 3 shows a fixed (preferably not part of the cartridge and reusable) sensor probe structure 170 configured to fit within the sensor sleeve 240. The sensor probe structure 170 includes a rigid outer tube 315 made from, e.g., stainless steel. Optical fibers 300 are disposed within the tube 315, and are configured to stimulate one or more fluorophores 250 disposed on a light transmissive outside lower wall portion 325 of sensor sleeve 240 and to receive fluorescent emissions from the fluorophore through the wall portion. When the probe is in its down position, it preferably forms a reduced media test volume in each well, as shown, for example, in FIG. 6b. As an alternative (not shown) probe sleeve 240 may comprise an annular wall portion extending below portion 325 which defines the reduced test volume. The sensor probe structure and fluorophore may be configured to read optical density, luminescence, phosphorescence, or, preferably, fluorescence. In an alternative embodiment (not shown) the sensor probe structure 170 may be a self contained sensor which gathers data from a well through a signal transmissive bottom wall of the sleeve 240, or directly through an open bottom on the sleeve, preferably sealed to the probe.

Various types of sensors can be utilized depending on the analysis to be performed and its selected configuration, including oxygen sensors, such as oxygen-quenched fluorescent sensors, pH sensors, including fluorescent sensors, ISFET and impedance sensors using electrodes coupled through bottom wall 325 of sleeve 240, $CO_2$ sensors, including bicarbonate buffer coupled and ammonium dye coupled fluorescent sensors as well as other $CO_2$ sensors; various ion and small molecule sensors; large molecule sensors including surface plasmon resonance sensors and sensors exploiting the principle of Wood's anomaly; acoustic sensors; and microwave sensors. In certain embodiments, a conventional plate reader may be used.

Preferred sensors are fluorophores. Many fluorescent sensing compounds and preparations are described in the art and many are available commercially from, for example, Molecular Probes Inc and Frontier Scientific, Inc. The currently preferred oxygen sensor is a fluorophore with the signal inversely proportional to oxygen concentration such as a porphyrin or rhodamine compounds immobilized as a particle or homogenously distributed in an oxygen permeable polymer, e.g., silicone rubber. The currently preferred compound is porphyrin. The currently preferred pH sensor is a fluorescent indicator dye, fluorescein, whose signal decreases upon protonation of the dye, and which is either entrapped in a particle that is suspended in a carrier polymer, or covalently attached to a hydrophilic polymer. Useful fluorescent CO2 indicator sensor typically are based on a pH sensitive transducer, with the fluorescence being indirectly modulated by the production of carbonic acid due to reaction of carbon dioxide with water. See, e.g. O. S. Wolfbeis, Anal. Chem. 2002, 74, 2663-2678. A fluorophore that detects glucose also can be used, such as one based on a non-enzymatic transduction using a boronic probe that complexes with glucose, resulting in a charge transfer that modulates the fluorescence of the probe, or an enzymatic glucose transducer that couples a glucose oxidase to a fluorescent oxygen sensor, with the binding and oxidation of glucose resulting in a quantitative modulation of the oxygen sensor. It also is within the scope of the invention to employ a fluorophore or other type of sensor sensitive to biological molecules such as, for example, lactate, ammonia, or urea. A lactate sensor can be based on an enzymatic sensor configuration, with lactate oxidase coupled to a fluorescent oxygen sensor, and with the binding and oxidation of lactate resulting in a quantitative modulation of the oxygen sensor. An ammonia or ammonium ion sensor can be configured with immobilization of a protonated pH indicator in a hydrophobic, gas permeable polymer, with the fluorescence output quantitatively modulated by reaction with transient ammonia. A urea sensor can be based on an enzymatic sensor configuration, with urease coupled to a fluorescent ammonia transducer, and with the binding and reduction of urea to ammonia, resulting in modulation of the ammonia sensor fluorescence.

In the illustrated embodiment, the fixed sensor probe 170 is attached to and extends orthogonally from the pneumatic multiplexer 150. Other sensor configurations will be apparent to those skilled in the art. For example, probes may be disposed on a wall within the well under examination, or on a bottom, translucent surface of a well.

Air channels 310 are defined within the pneumatic multiplexer 150 and are positioned to feed drug wells or ports 230 when the elongated neck of the fixed sensor probe 315 is fitted within with the sleeve 240. The pneumatic multiplexer 150 serves to deliver compressed gas to a plurality of ports (see FIG. 6a) from a single source that may be controlled by an electrical or mechanical gas regulator or valving. Other types of pneumatic, mechanical or hydraulic pressure actuators may be used. For example, the actuator may be a piston within a sleeve, as described in U.S. Pat. No. 4,498,510 to Minshew et al., or a controlled gas supply as described in U.S. Pat. No. 4,461,328 to Kenney, or any other suitable means for ejecting liquid test compound from the bottom of the port 230 using an extrinsic force.

The use of a pneumatic multiplexer may be preferable for the sake of simplification and reduction of the number of components that supply compressed gas to the apparatus. The currently preferred pneumatic multiplexer 150 is discussed in greater detail below.

Referring to FIG. 4, a region 210 of the cartridge 110 includes first and second ports 230. In use, a test compound such as a drug, drug candidate, toxin, etc. is added to the ports 230 of cartridge 110 before beginning an analysis using a pipettor or other means. The compound typically will be an aqueous solution of a known concentration. In preferred embodiments, it is held within each port despite the presence of a small outlet at its bottom by surface tension. The dimensions of the port inhibit leakage from the bottom and from the top end (forming a meniscus that prevents leakage if the apparatus is turned on its side or upside down). The test compound may be released by, e.g., the application of pressurized air.

It may be desirable to operate the apparatus with test liquids that are difficult to contain using capillary force due to their relatively low viscosity or electrostatic properties. In this case, a frangible membrane or a fragile material, such as wax may be attached to cover the hole in the bottom of the port 230, such that an extrinsic force can breach the membrane to eject the liquid at a desired time.

In the depicted embodiment, the submersible sleeve 240 is disposed between first and second ports 230. Sensors 250, e.g., fluorophores, are disposed on surface 325 at the lower end of the sleeve. The submersible sleeve 240 is configured to receive the sensor probe 170.

An array of integrated sensor sleeves and compound storage and delivery ports may be fabricated as a single assembly using a low cost fabrication process such as injection molding so that the cartridge may be disposed of after use.

Referring to FIG. 5, the well 220 is formed of, e.g., molded plastic, such as polystyrene or polypropylene. In use, cell media 500 and live cells 510 are disposed in the well 220. Cells 510 may or may not adhere to a bottom surface 520 of the well, and the bottom surface may be treated or coated to encourage adherence. Alternatively, cells may be suspended within the media.

Referring to FIGS. 6a and 6b, in use, when the parts are assembled, they allow simultaneous sensing of constituents in the cell media in plural wells simultaneously, and delivery of test compound from the ports.

As illustrated, the fixed probe structure and drug loaded cartridge are assembled such that the outer tubing holding the fiber optic bundle is disposed within the sleeve of the cartridge, and the assembly is reciprocated from an up position, where the probe tip and sensors are disposed in the cell medium, to a lower, data gathering position, preferably one that reduces the volume of media about the cells so as to improve the ability of the sensor to detect changes in the concentration of an analyte in the media about the cells (see US 2005/0054028). In the preferred embodiment, the sensors 250 disposed on the lower surface 325 of the sensor sleeve 240 remains submerged during mixing, equilibrating, and measurement steps. One or more constituents within the media secreted from or absorbed by the cells may by analyzed. In a first lowered position (FIG. 9a), a fluid, such as a drug sample, is delivered from one of the ports 230 to the cell medium, in this embodiment impelled by air pressure communicated through air channels 310. As noted above, the drug may be released through a small hole disposed at a bottom portion of the port 230.

After the fluid is dispensed into the media, the sensor sleeve 240 may be raised and lowered one or more times while remaining submerged in the media to mix the fluid with the media. The sensors 250 may remain disposed within the media during the dispensing and mixing steps, thereby reducing stabilization periods.

After the test fluid is dispensed and mixed with the media, the sensors 250 and sensor sleeve 240 are lowered to a second lower position in the well 220. A bottom portion of the well 220 may include a seating surface for the sensor sleeve 240, e.g., an internal step defining a step plane above a bottom plane of the well 220, the step plane and bottom plane being parallel planes. In a microwell microplate, the height of the step plane may generally be less than about 1 mm above the bottom plane and typically less than about 50 µm to 200 µm above the bottom plane. Alternatively, a flat bottomed well or other well configuration may be used, and the fluorophore probes may disposed on surface 255 within a recess formed by a wall extending slightly beyond the surface as disclosed above. In either case, in this embodiment a small volume subchamber is formed about cells when the assembly is disposed in a down position. Relatively small changes in the concentration of the constituent than can be detected by the fluorophore probes, as the measurement is taken within the confines of a much smaller volume of medium. This subvolume is maintained for a short time period to make a measurement, and the assembly is moved upwardly, permitting the cells to be exposed to the full well volume of its medium.

In an alternative embodiment, the test fluid from the port may be delivered to the media when the sensor sleeve in the partially raised, but still submerged position.

During or after the delivery of the test fluid to the well, the constituent in the medium may be analyzed to determine any changes, and the measurements can be repeated with or without intermediate addition of test compounds. Any number of constituents of the media may be analyzed, including dissolved gasses, ions, proteins, metabolic substrates, salts, and minerals. These constituents may be consumed by the cells (such as $O_2$), or may be produced by the cells either as a byproduct (such as $CO_2$ and $NH_3$) or as a secreted factor (such as insulin, cytokines, chemokines, hormones, or antibodies). Ions such as $H^+$, $Na^+$, $K^+$, and $Ca^{++}$ secreted or extracted by cells in various cellular metabolism processes may also be analyzed. Substrates either consumed or produced by cells such as glucose, fatty acid, amino acids, glutamine, glycogen, and pyruvate may be analyzed. Specialized media may be used to improve the sensitivity of the measurement. For example, a change in pH resulting from extracellular acidification can be increased by using a media with reduced buffer capacity, such as bicarbonate-free media.

The method may be used to measure any number of attributes of cells and cellular function. For example, cell viability and metabolic rate may be determined from measurements of oxygen consumption rate, extracellular acidification rate, or other metabolic analyte fluxes. By comparison of one or more analyte flux rates to a known rate per cell, cell number may be determined and therefore growth rates can be monitored.

The introduction of an environment altering constituent such as a chemical, dissolved gas, or nutrient may be applied to either the full volume of the well or alternatively to only the reduced volume of the well. In the latter embodiment, the volume of media surrounding the cells is first reduced, the constituents of the media are measured, and the volume is restored to its original value. The volume is then again reduced and the environment immediately surrounding the cells within only the reduced volume is then altered, by the addition of a constituent from one of the four corresponding ports. This may be accomplished by discharging the constituent from a port proximate the sensors or the bottom of the sleeve, for example. One or more measurements in the reduced volume are made in the presence of the constituent. After this measurement cycle, the media within the reduced volume may be exchanged one or more times to flush out the constituent before exposing cells once again to the full original volume. This approach may provide a benefit of reducing the volume of compound required. It may also provide the possibility of studying isolated effects without contaminating the entire volume, thereby, in effect, simulating a flow system in microplate format.

In preferred embodiments, as illustrated in the drawing, a plurality of sensors are inserted and disposed simultaneously or sequentially in a corresponding plurality of wells in the multiwell plate, and constituents related to respective cell cultures in respective wells are analyzed. The respective constituents may include the same constituent. Respective test fluids may be delivered to the respective wells while the respective sensors remain in equilibrium with, preferably remain disposed within the media in respective wells. It is possible to maintain equilibrium with many sensors, particularly fluorophore sensors, while the sensor body is removed from the media for a short time, e.g., if the probe remains wetted, permitting maintenance of equilibrium while adding test fluid. In one embodiment, the respective test fluids may be the same test fluid. The respective constituents related to respective cells within media in respective wells may be analyzed to determine any respective changes therein. These delivery and analysis steps may be repeated. In another embodiment, the delivery step is repeated with a different test fluid.

In some instances, the delivery and analysis may be repeated after a time period. More particularly, sequential measurements of a single group of cells may be made at predetermined time intervals to analyze the effect of a compound addition temporally, for example to examine the effect of exposure to a drug, chemical, or toxin. In this method, the volume of media surrounding the cells is first reduced, the constituents of the media are measured, and the volume is restored to its original value. The environment surrounding the cells is then altered, such as by adding one or more predetermined concentrations of a ligand that activates a transmembrane receptor, changing the dissolved oxygen level, or adding a nutrient. One or more additional measurement cycles then are performed using the temporarily reduced volume method, to analyze the effect of the altered extracellular environment.

Equilibration between the sensor and the media may be maintained during the delivery step. Thermal equilibrium may be substantially maintained between the test fluid and media during the delivery.

Figure 7:
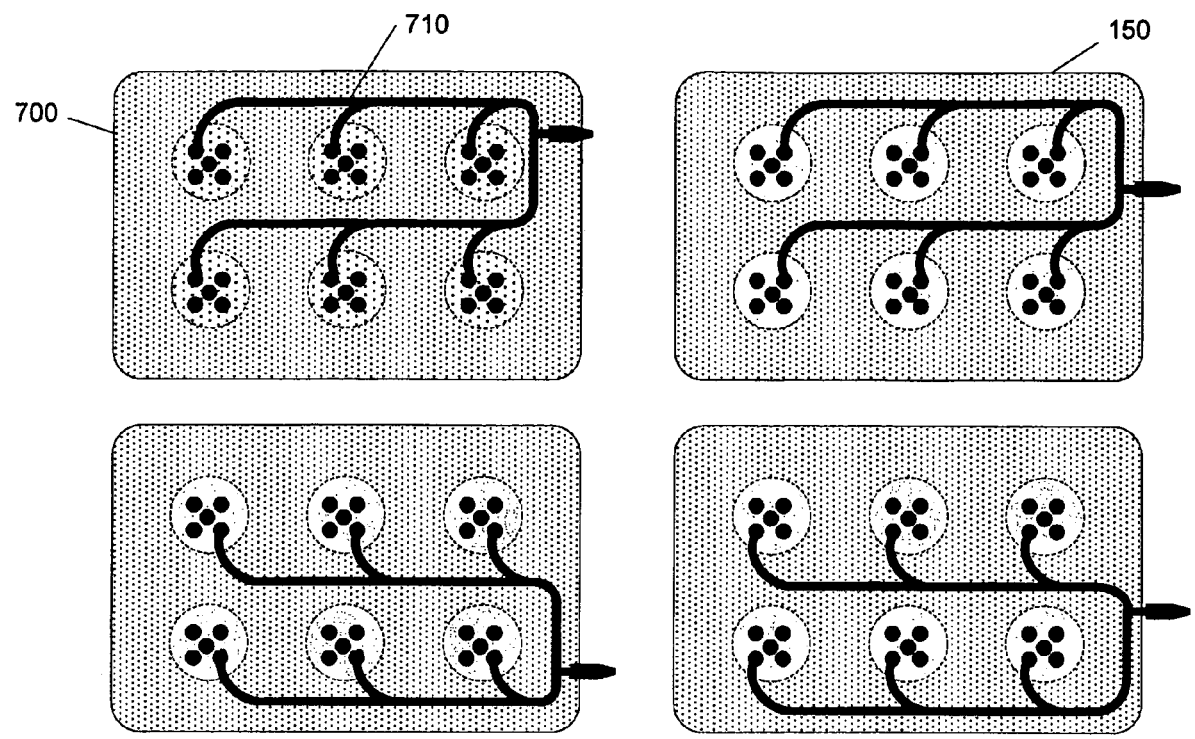
FIG. 7 is a schematic top view of four layers of a microfabricated pneumatic multiplexer, a portion of which is shown in FIG. 3.
Figure 8:
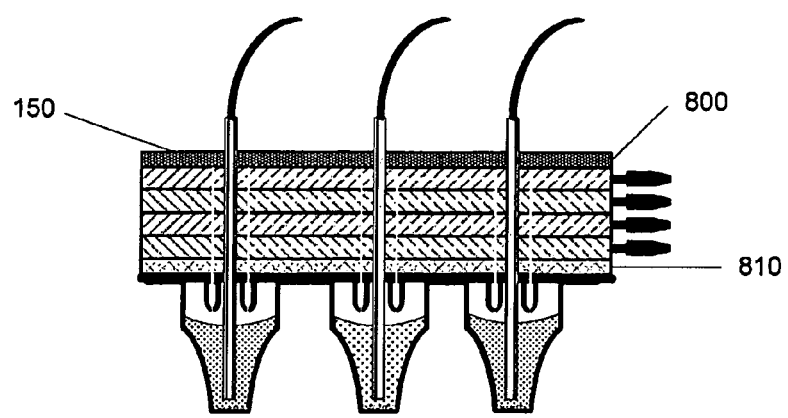
FIG. 8 is a schematic cross-sectional view of three regions each comprising a probe, a portion of a cartridge, and a well in combination with the pneumatic multiplexer of FIG. 7.

Referring to FIGS. 7 and 8, the currently preferred form of the multiplexer 150 is shown. It comprises a laminated assembly of multiple layers 700 of planar polymeric sheet material containing machined channels 710 for gas flow, sandwiched between a cover sheet 800 and cartridge facing gasket 810. One such arrangement uses four layers, e.g., four machined blocks placed in different orientations, to create a pneumatic multiplexer enabling the dispensing of fluid from any one of four ports disposed in each region of the cartridge. The multiplexer enables the delivery of gas from a single gas inlet to multiple outlets. In use, the multiplexer is disposed between a pressure source and the cartridge, with the multiplexer adapted to be in fluidic communication with a plurality of ports formed in the cartridge. The multiplexer may be selectively in fluidic communication with an exclusive set of ports formed in the cartridge.

Figure 9:
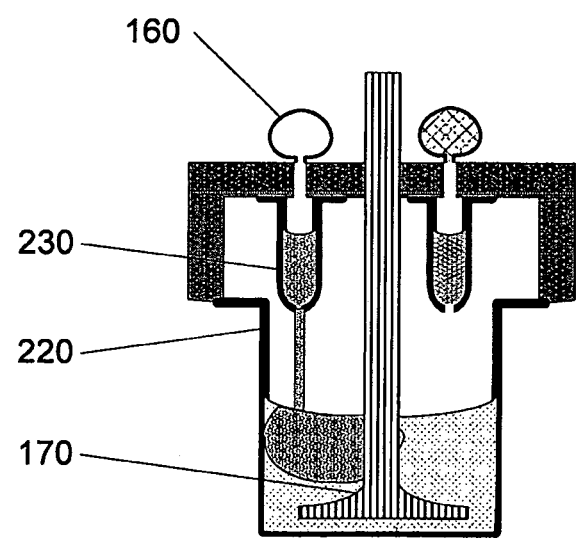
FIG. 9 is a schematic view of a sensor probe submerged in the liquid media contained within a microplate well.

\Referring to FIG. 9, the sensor probe 170 is depicted submerged in the liquid media contained within a microplate well 220. The drug delivery apparatus is shown activated using gas pressure from the pressurized gas supply 160 to deliver a drug from the port 230 to the media.

Figure 10:
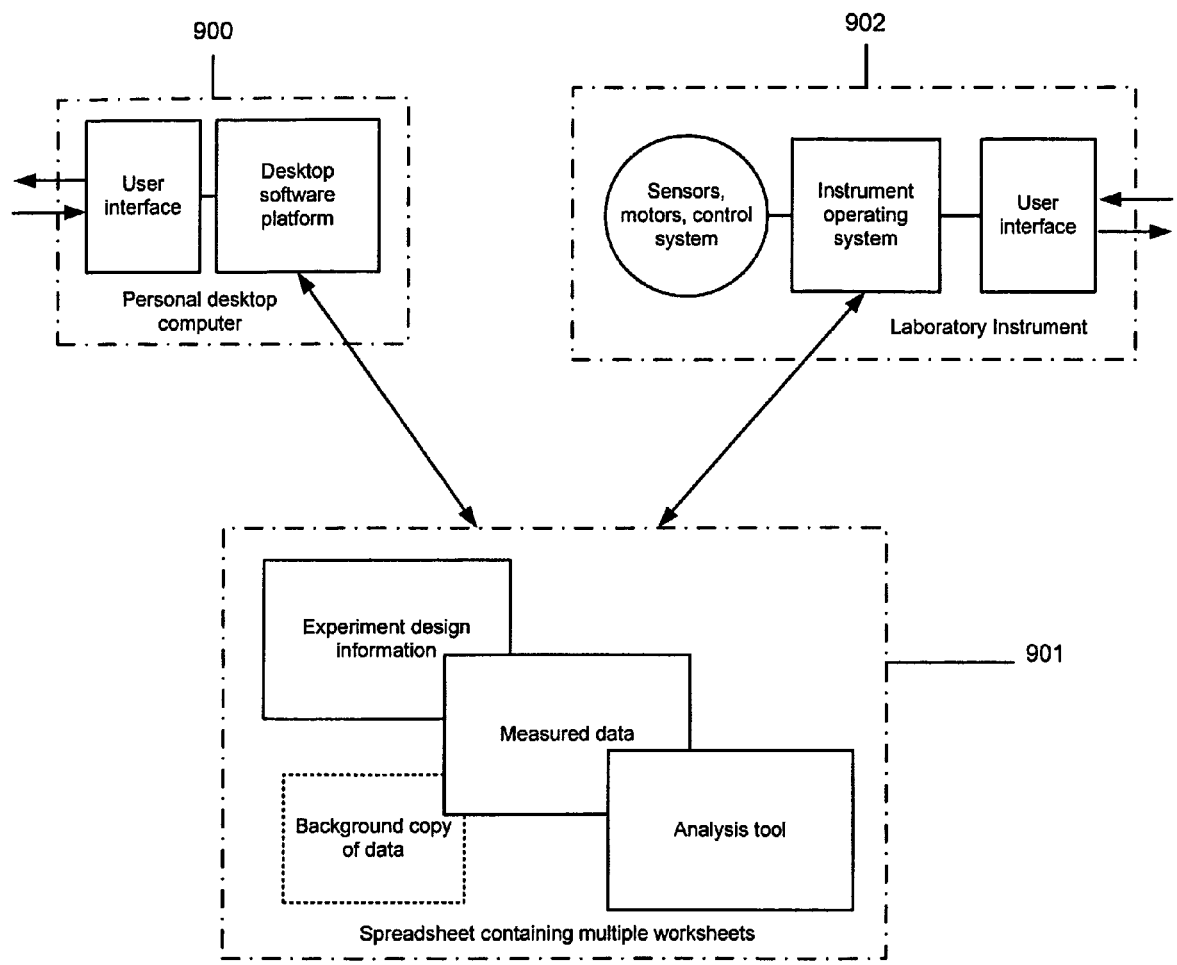
FIG. 10 is a block diagram of an embodiment of a system according to the invention.

FIG. 10 schematically illustrate one embodiment of the invention realized as an instrument and software for analyzing cells undergoing various experimental processes using any of the techniques described above. A key element of the invention is a data file shared by instrument operating system running on the embedded instrument computer, and desktop software running on a user's personal desktop computer.

As illustrated in FIG. 10, Desktop software 900 contains a user interface that allows a user to enter experiment design information into data file 901. Experiment design information may include the type of cells, number of cells, type of drug, and concentration of drug contained in each microplate well, the required measurement time, media mixing time, the analyte to be assayed, or other data that define attributes of the experiment to be run by the instrument.

Instrument operating system software 902 both receives experiment design information from, and stores experiment results to, data file 901. Operating system software 902 also contains a user interface for viewing and modification of experiment design information and for viewing of experiment results.

The instrument operating system software provides actuation and control of motors, heaters and other devices based on the settings provided in the data file. During each measurement cycle, measured data may be displayed on the user interface and concurrently added to the data file. At the end of a complete experiment, the data file, containing experiment definition data, and measured sensor data, may be stored and transmitted to the user's desktop computer for analysis. The user may a third-party analysis software package that draws data from the data file. Examples of suitable third-party analysis software include MICROSOFT EXCEL (Microsoft Corp), JMP (SAS Corp), and SIGMA PLOT (Systat Corp).

In a preferred embodiment, data file 901 is in the form of a spreadsheet.

In another preferred embodiment, data file 901 contains experiment design information and experiment results as separate worksheets within one spreadsheet file.

In another preferred embodiment, data file 901 contains experiment design information, experiment results, and a data analysis tool, each as separate worksheets within one spreadsheet file.

Data file 901 may be formatted as a workbook file for use within a spreadsheet software application such as Microsoft Excel.

Further, in a preferred embodiment of the data file, the experiment definition information and instrument-generated data may be duplicated and additionally saved in machine-readable binary format on a separate hidden, password-protected area within the file. This capability preserves the integrity of the original data while changes are made by the user for analysis.

In another embodiment, proprietary binary data packets may be passed directly to other software configurations encoded with the custom graphical user interface and display areas. These alternative software environments might include traditional Windows or Macintosh applications, stand-alone executable files with the embedded binary data, web browser applications configured to load and display the data, or other viewing environments.

Figure 11:
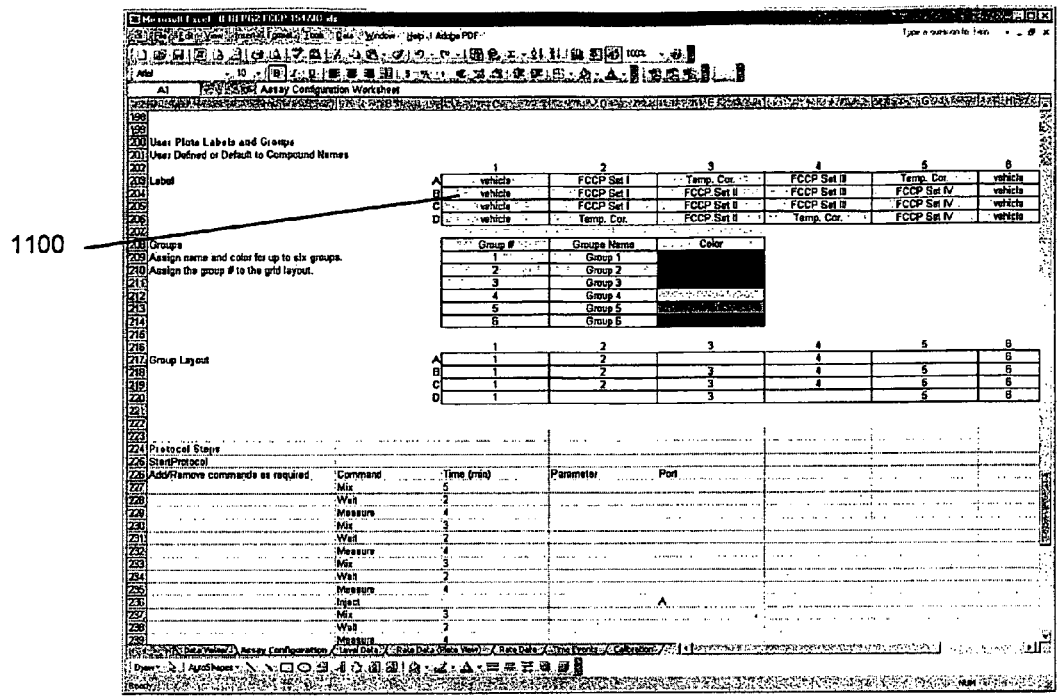
FIG. 11 is one example of a screen display of one embodiment of the system of FIG. 10.
Figure 12:
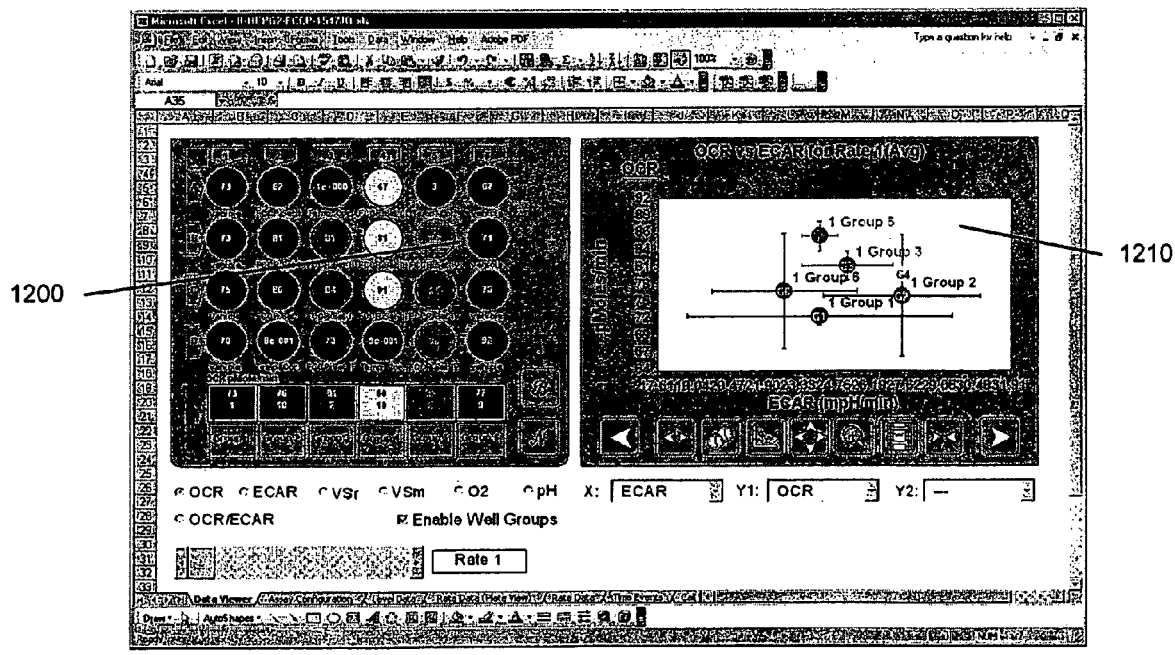
FIG. 12 is another example of a screen display of one embodiment of the system of FIG. 10.

Referring to FIGS. 11 and 12, the system includes a graphical user-interface for accepting instructions relating to the experiments and presenting results therefrom. Specifically, and in one embodiment, graphical user interface 1100 includes multiple display areas (e.g., cells in a spreadsheet program in which each cell can be individually addressed using row and column designators). Each display area may, for example, represent one of the wells in a microplate, thus providing data specific to the cells in each well, and in some cases also include various parameters of the experiment and/or results of the experiment based, for example, on signals received from the probes 170. In embodiments in which multiple microplates are used simultaneously (or substantially simultaneously), inputs, parameters and/or results of the experiments from the different wellplates may be presented using multiple spreadsheets, such as tabbed worksheets in EXCEL.

In some embodiments, the system also includes an analysis module for producing graphical representations and/or statistical analysis of the data acquired by the probes and presented within the user interface. Referring to FIG. 12, the results of the experiments, as well as the outputs (both graphical and textual) can also be represented within user-interface 1200. For example, individual icons, images (e.g., GIF files, JPEG files) or colorations of display areas can be used to represent the current (or most recently measured) pH of an assay, and a graphical display can be used to represent the same measurement (or others) over time.

In a preferred embodiment, the results of an experiment may be presented to the user in the form of a chart having data from each of two sensors shown on each of two axes. For example, oxygen consumption rate may be displayed on the ordinate while extracellular acidification rate is shown on the abscissa. As shown in FIG. 12, chart 1210 displays data from each well of a multi-well experiment as a dot with an associated label and error bar set.

EXAMPLES

The following examples illustrate certain exemplary and preferred embodiments and applications of the instant invention, but are not intended to be illustrative of all embodiments and applications.

Example 1

Evaluation of a 96 Well Drug Delivery Cartridge and Pneumatic Multiplexer

Probes incorporating four drug wells or ports were fabricated from polystyrene material using injection molding. Twenty four probes were then bound together using an elastomeric sheet to form a single 4"×6" cartridge unit that is suitable for use as a disposable measurement and drug delivery assembly. A pneumatic multiplexer was fabricated by machining gas channels in four polystyrene blocks, then bonding these layers together and applying a cover. The multiplexer was then clamped to the cartridge.

50 µl of water containing a colored dye was introduced to each of the 96 drug wells using an automated pipetting system (Biotec 2000). A gas (air) accumulator was pressurized to 15 psi. Gas hoses were used to supply air from the accumulator to four electrically actuated solenoid valves. Each valve was mounted on the multiplexer, and the multiplexer gas channels were arranged such that actuation of a single solenoid would provide gas flow to 24 of the 96 drug wells.

The cartridge and multiplexer assembly was then placed above a 24 well microplate reservoir (Innovative Microplate). An electrical drive circuit was configured to actuate each solenoid for 250 µsec in order to deliver the fluid from the drug wells.

Upon first actuation of the solenoids, nearly complete delivery of water was observed in 20 of the 24 wells. The second, third and fourth solenoid were then actuated, giving similar results.

A silicone rubber seal was then inserted between the multiplexer and the cartridge, and the experiment was repeated.

Complete injection of fluid from 24 wells was observed when the first and second solenoid were actuated. Some residual water was seen in several wells actuated by the third and fourth solenoid.

The accumulator pressure was then reduced to 5 psi, and was recharged between sequential actuation of solenoids one through four. The electronic circuit was then adjusted to increase the actuation time to 275 µsec. In this case, complete injection of water was noted for each of the 96 drug wells.

Example 2

Performance Measurement of a 96 Well Drug Delivery Cartridge and Pneumatic Multiplexer A test was performed using the components and method described in Example 1, except that a mixture of saline solution and Tartrazine was substituted for water in the drug wells. The fluid was injected into a microplate reservoir, and then the absorbance of the contents of each well in the reservoir was measured using a Molecular Devices Versamax microplate reader. Absorbance readings indirectly measure dye injection volume and demonstrate injection performance.

The experiment was performed with and without a flexible seal between the multiplexer and cartridge, and three volumes of saline/Tartrazine (50, 75 and 100 µl) were injected. The resulting absorbance values are shown in Table E1.

TABLE E1

Absorbance measurements for injection of Tartrazine dye into water using pneumatic multiplexer

| | Injection Performance Test 1 | | | | | | | Injection Performance Test 2 | | | | | |
|---|---|---|---|---|---|---|---|---|---|---|---|---|---|
| | Column | | | | | | | Column | | | | | |
| Row | A | B | C | D | E | F | Row | A | B | C | D | E | F |
| | 50 uL Tartrazine | | | | | | | 50 uL Tartrazine | | | | | |
| 1 | 0.223 | 0.222 | 0.269 | 0.244 | 0.223 | 0.219 | 1 | 0.222 | 0.222 | 0.234 | 0.220 | 0.216 | 0.223 |
| 2 | 0.225 | 0.232 | 0.226 | 0.228 | 0.221 | 0.229 | 2 | 0.221 | 0.225 | 0.223 | 0.226 | 0.226 | 0.223 |
| 3 | 0.225 | 0.216 | 0.219 | 0.219 | 0.221 | 0.222 | 3 | 0.211 | 0.216 | 0.220 | 0.215 | 0.237 | 0.230 |
| 4 | 0.219 | 0.219 | 0.221 | 0.248 | 0.223 | 0.222 | 4 | 0.222 | 0.222 | 0.225 | 0.223 | 0.221 | 0.223 |
| | 75 uL Tartrazine | | | | | | | 75 uL Tartrazine | | | | | |
| 1 | 0.305 | 0.300 | 0.282 | 0.289 | 0.326 | 0.296 | 1 | 0.326 | 0.300 | 0.320 | 0.317 | 0.319 | 0.314 |
| 2 | 0.292 | 0.282 | 0.292 | 0.281 | 0.285 | 0.292 | 2 | 0.311 | 0.309 | 0.310 | 0.310 | 0.314 | 0.308 |
| 3 | 0.277 | 0.279 | 0.274 | 0.284 | 0.282 | 0.281 | 3 | 0.308 | 0.301 | 0.310 | 0.307 | 0.314 | 0.318 |
| 4 | 0.282 | 0.279 | 0.329 | 0.282 | 0.284 | 0.293 | 4 | 0.308 | 0.308 | 0.313 | 0.319 | 0.317 | 0.307 |
| | 100 uL Tartrazine | | | | | | | 100 uL Tartrazine | | | | | |
| 1 | 0.349 | 0.345 | 0.343 | 0.343 | 0.339 | 0.335 | 1 | 0.358 | 0.385 | 0.357 | 0.346 | 0.350 | 0.356 |
| 2 | 0.340 | 0.332 | 0.338 | 0.340 | 0.343 | 0.342 | 2 | 0.365 | 0.343 | 0.359 | 0.348 | 0.353 | 0.357 |
| 3 | 0.342 | 0.342 | 0.336 | 0.335 | 0.339 | 0.337 | 3 | 0.349 | 0.346 | 0.351 | 0.349 | 0.357 | 0.353 |
| 4 | 0.345 | 0.295 | 0.345 | 0.344 | 0.355 | 0.348 | 4 | 0.358 | 0.349 | 0.357 | 0.355 | 0.353 | 0.352 |

| Tartrazine qty | Mean absorb | Std Dev | c.v. | Tartrazine qty | Mean absorb | Std Dev | c.v. |
|---|---|---|---|---|---|---|---|
| 50 ul | 0.23 | 0.0118 | 5.2% | 50 ul | 0.22 | 0.0056 | 2.5% |
| 75 ul | 0.29 | 0.0139 | 4.8% | 75 ul | 0.31 | 0.0061 | 2.0% |
| 100 ul | 0.34 | 0.0108 | 3.2% | 100 ul | 0.35 | 0.0083 | 2.3% |

Example 3

Metabolic Rate Assay Using a 96 Well Drug Delivery Cartridge and Pneumatic Multiplexer A test was performed using the components described in Example 1, and a 24 well microplate containing $30 \times 10^3$ HEP-G2 human hepatocellular liver carcinoma cells per well. Three initial "baseline" measurements of cellular oxygen consumption rate (OCR) and extracellular acidification rate (ECAR) were performed at eleven minute intervals using a 4 minute measurement period.

70 μL of FCCP, from one of the four injector ports, was then added to each well containing 630 μL of media and cells using the method described in example #1, followed by measurement of OCR and ECAR. This was repeated three additional times using the second, third and fourth injector ports. Two control columns, A and F, were injected four times with vehicle only. Columns B, C, D and E contained three replicate wells receiving 4 injections of either a low (FIG. 13a, aqua), medium-1 (FIG. 13b, orange), medium-2 (FIG. 13c, pink) or high (FIG. 13d, blue) dose series of FCCP. The final concentration of FCCP in the well is shown above each graph for each injection, A-D. The cumulative addition of FCCP stock concentrations from each injector port followed by measurement of OCR and ECAR enabled a four-point dose curve to be generated in each well.

Figure 13:
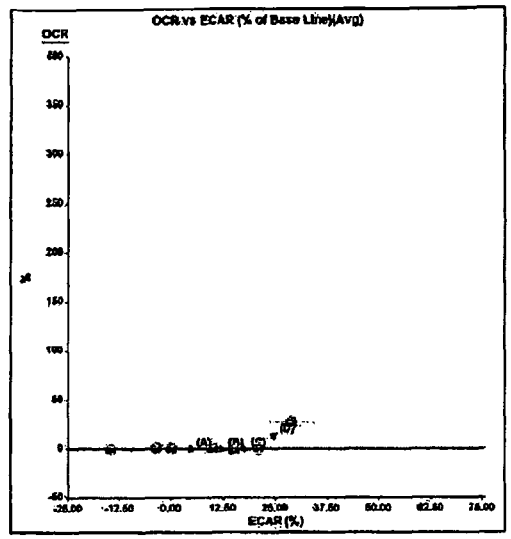
FIGS. 13a, 13b, 13c, and 13d are graphs illustrating the results of monitoring metabolic rates in accordance with an embodiment of the invention.
Figure 13:
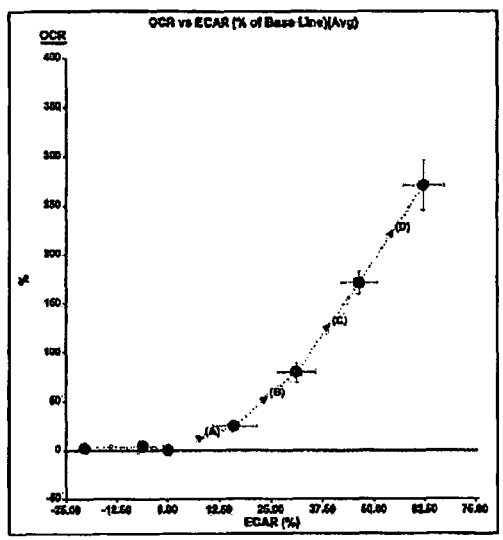
Figure 13:
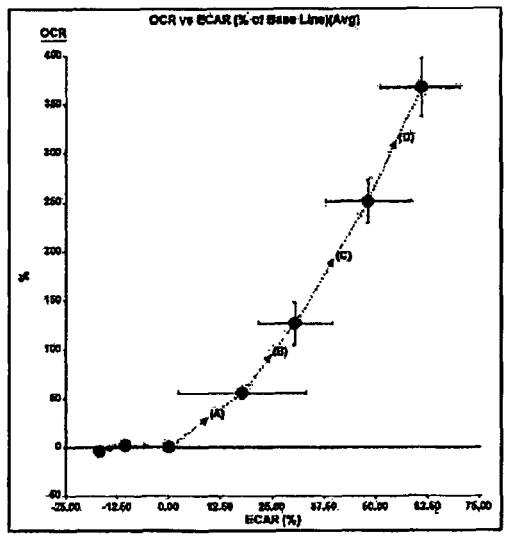
Figure 13:
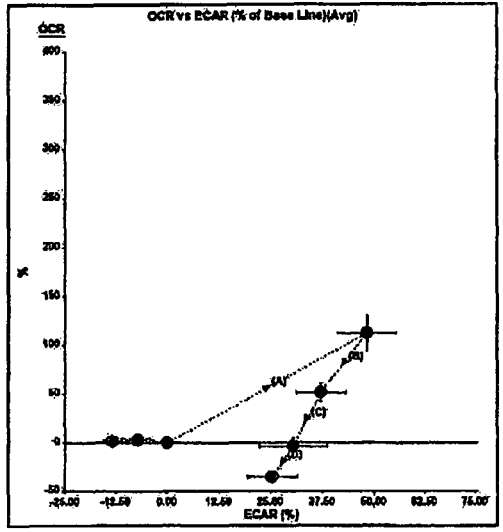

FCCP induces mitochondrial uncoupling and causes cells to increase their metabolic rate and therefore OCR and ECAR. As demonstrated in FIG. 13, depending on the final concentration of FCCP, each series produced either no or an increasingly higher OCR and ECAR response until toxicity was reached as demonstrated in the high dose series (FIG. 13d). By measuring OCR and ECAR simultaneously the total metabolic rate and capacity of the HepG2 cells could be determined. By being able to cumulatively add increasing concentrations of FCCP several dose curves can be generated in a single assay while minimizing well-to-well variation inherent in all cell-based assays.

The invention may be embodied in other specific forms without departing from the spirit or essential characteristics thereof. The foregoing embodiments are therefore to be considered in all respects illustrative of the invention described herein. Various features and elements of the different embodiments can be used in different combinations and permutations, as will be apparent to those skilled in the art. Scope of the invention is thus indicated by the appended claims rather than by the foregoing description, and all changes which come within the meaning and range of equivalency of the claims are therefore intended to be embraced herein.

What is claimed is:

1. A high-throughput cellular assay method comprising the steps of:
    disposing cells in media in multiple wells of a multiwell plate;
    moving into the medium in multiple wells at least a portion of sensors configured to sense the concentration of a dissolved constituent absorbed by or secreted from cells in the medium in the wells;
    delivering to multiple wells a test fluid from test-fluid-containing ports disposed in a cartridge above the respective wells while the sensors are disposed in the medium in the wells; and
    measuring within the medium the presence or concentration of said dissolved constituent in multiple wells by detecting signals from the sensors disposed in the medium; and
    determining a property of the cells in the respective well on the basis of the measured presence or concentration of said dissolved constituent.

2. The method of claim 1 wherein the test fluids are delivered to each of the multiple wells simultaneously, and the concentrations of constituents are measured in each of the multiple wells simultaneously.

3. The method of claim 1 wherein the same constituent is measured in each of the multiple wells.

4. The method of claim 1 wherein multiple constituents are measured in the multiple wells.

5. The method of claim 1 wherein the test fluids in respective wells comprise the same test fluid.

6. The method of claim 1 further comprising repeating the delivering and the detecting steps after a first detection.

7. The method of claim 6 wherein a different test fluid is delivered after the first detection.

8. The method of claim 1 comprising maintaining substantially thermal and constituent concentration equilibrium between the sensors and the media during the delivery step.

9. The method of claim 1 wherein the sensors comprise a fluorescent sensor.

10. The method of claim 1 wherein each of the test fluids comprises at least one of a drug, a drug candidate, a toxin, or a nutrient.

11. The method of claim 10 further comprising repeating the delivering and the detecting steps after a first detection, using second test fluids comprising different concentrations of at least one of a drug, a drug candidate, or a toxin.

12. The method of claim 10 wherein a concentration of the at least one of a drug, a drug candidate, or a toxin is known prior to delivery of the test fluid.

13. The method of claim 1 wherein the constituent is selected from the group consisting of $CO_2$, $O_2$, $H^+$, $Ca^{++}$, $NH_3$, $Na^+$, and $K^+$.

14. The method of claim 1 wherein the constituent is selected from the group consisting of cytokines, chemokines, hormones, antibodies, glucose, fatty acids, amino acids, glutamine, glycogen, and pyruvate.

15. The method of claim 14 wherein the hormones comprise insulin.

16. The method of claim 1 wherein the media are bicarbonate-free.

17. The method of claim 1 wherein the cells comprise animal cells.

18. The method of claim 1 wherein the sensors comprise an electrochemical sensor.

19. The method of claim 1 wherein the property of the cells comprises at least one of cell viability or metabolic rate.

20. The method of claim 1 wherein delivering test fluids to the multiple wells comprises delivering test fluids having different concentrations of a drug, a drug candidate, or a toxin to multiple wells.

21. The method of claim 1 wherein delivering test fluids to the multiple wells comprises pressurizing the test-fluid-containing ports.

22. The method of claim 1 wherein the cartridge defines a plurality of sensor sleeves and the sensors are disposed on the sensor sleeves.

23. The method of claim 1 wherein the cartridge defines a plurality of sensor sleeves adapted to receive the sensors.

* * * * *